US00PP07761P

United States Patent [19]

Saville

[11] Patent Number: Plant 7,761

[45] Date of Patent: Jan. 7, 1992

[54] MINIATURE ROSE PLANT NAMED SAVAGOOD

[75] Inventor: F. Harmon Saville, Rowley, Mass.

[73] Assignee: Nor'East Miniature Roses, Inc., Rowley, Mass.

[21] Appl. No.: 570,620

[22] Filed: Aug. 21, 1990

[51] Int. Cl.[5] ..... A01H 5/00

[52] U.S. Cl. ..... Plt./8

[58] Field of Search ..... Plt. 7, 8

*Primary Examiner*—James R. Feyrer

*Attorney, Agent, or Firm*—Christie, Parker & Hale

[57] ABSTRACT

A new and attractive miniature rose producing yellow flowers.

1 Drawing Sheet

SUMMARY OF THE INVENTION

The present invention relates to a new and distinct variety of rose plant of the miniature rose class, which was originated by my crossing as seed parent the variety known as "Fantasia" and as pollen parent the variety known as "Rainbow's End" (U.S. Plant Pat. No. 5,482). The varietal denomination of this new rose is "Savagood".

Among the novel characteristics possessed by this new variety which distinguishes it from its parents and all other varieties of which I am aware are its many petalled, attractive yellow flowers in this case of rose. Flowers open well despite the heavy petalage.

Asexual reproduction by propagation by cuttings of the new variety as performed in Essex County, Mass. shows that the foregoing and other distinguishing characteristics come true to form and are established and transmitted through succeeding propagations.

BRIEF DESCRIPTION OF THE DRAWING

The accompanying drawing shows typical specimens of the vegetative growth and flowers of the new variety in different stages of development and depicted in color as nearly true as it is reasonably possible to make the same in a color illustration of this character.

DESCRIPTION OF THE PREFERRED EMBODIMENT

The following is a detailed description of my new variety, with color terminology in accordance with The Royal Horticultural Society Colour Chart (R.H.S.C.C.). The terminology used in color description herein refers to plate numbers in the aforementioned color chart, e.g., "15B" is plate "15B" of The Royal Horticultural Society Colour Chart.

Parentage: Seedling.

*Seed parent.*—"Fantasia".

*Pollen parent.*—"Rainbow's End".

Class: Miniature.

The following observations are made of specimens grown under glass in Essex County, Mass., during the month of May.

FLOWER

Blooming habit: Recurrent, continuous.

A. Bud:

(1) *Size.*—Large for a miniature.

(2) *Form.*—Urn shaped.

(3) *Color.*—As sepals divide, bud color is from near 15B, C to near 16A.

(4) *Sepals.*—Longer than bud, slightly foliated.

(5) *Penduncle.*—Length — about 1 inch. Aspect — straight. Strength — erect. Color — near 144C.

B. Bloom:

(1) *Size.*—Average size when fully expanded — about 1½ inches.

(2) *Borne.*—Singly, one to a stem and in sprays of 6 to 12 blooms.

(3) *Form.*—High centered at first, becoming flat; petals quill to points and loosely roll under.

(4) *Petalage.*—Number of petals under normal conditions — about 55 to 60.

(5) *Color.*—After sepals fall and petals unfurl, predominant flower color viewing petals' top surface is from near 16C to near 16A. Color of petal undersurface tends toward the deeper tones of this range and shows lighter yellow hues, at least at the outer segments of outer petals, ranging from near 13D to near 16D with some white highlights. General tonality at a distance is an attractive medium yellow. Color of petals at point of attachment is near 12A. Flower coloring on outdoor grown plants may range from 13C to 13B. As blooms age, yellow tones of outer petals lighten to near 12D.

C. Petals:

(1) *Texture.*—Thick.

(2) *Appearance.*—Inside velvety and outside satiny.

(3) *Form.*—Broad, fan shaped with pointed apices.

(4) *Arrangement.*—Regularly arranged, imbricated.

(5) *Petaloids in center.*—Few.

(6) *Persistence.*—Average.

(7) *Fragrance.*—Moderate, fruity.

(8) *Lasting quality.*—Very long lasting quality on plant.

REPRODUCTIVE ORGANS

A. Stamens, filaments and anthers:

*Arrangement.*—Regularly arranged around styles.

*Color.*—Filaments near 14A.

B. Pollen:

*Color.*—Near 15A.

C. Styles: Uneven length.

D. Stigmas:

*Color.*—Near 7B.

E. Hips: None observed.

PLANT

A. Form: Upright.

B. Growth: Very vigorous for a miniature.

*Height attained.*—About 20 to 25 inches.

C. Foliage: Compound 5 to 7 leaflets.

(1) *Size.*—Medium.

(2) *Quantity.*—Abundant.

(3) *Color.*—New foliage: Upper side — near 146B. Under side — near 139C. Old foliage: Upper side — near 137A. Under side — near 138B.

(4) *Shape.*—Oval, pointed.

(5) *Texture.*—Upper side is semi-glossy; under side is matte.

(6) *Edge.*—Serrate.

(7) *Serration.*—Even and moderate; deeper at leaf apex point.

(8) *Leaf stem.*—Color — near 183A. Under side — 195A.

(9) *Stipules.*—Medium length, not noticeably bearded.

(10) *Resistance to disease.*—Blackspot — Good. Mildew — Good. Rust — Good.

D. Wood:

(1) *New wood.*—Color — near 144C. Bark — smooth.

(2) *Old wood.*—Color — near 138A. Bark — smooth.

E. Thorns:

*Quantity (main stalk).*—Ordinary.

*On laterals from stalk.*—Few.

*Form.*—Long, thin, angled slightly downward.

*Length.*—Medium.

*Color.*—Near 186A.

*position.*—Irregular.

*Prickles.*—None.

F. Winter hardiness: Needs protection in severe climates.

I claim:

1. A new and distinct variety of rose plant of the miniature rose class, substantially as shown and described, characterized particularly by attractive yellow flowers.

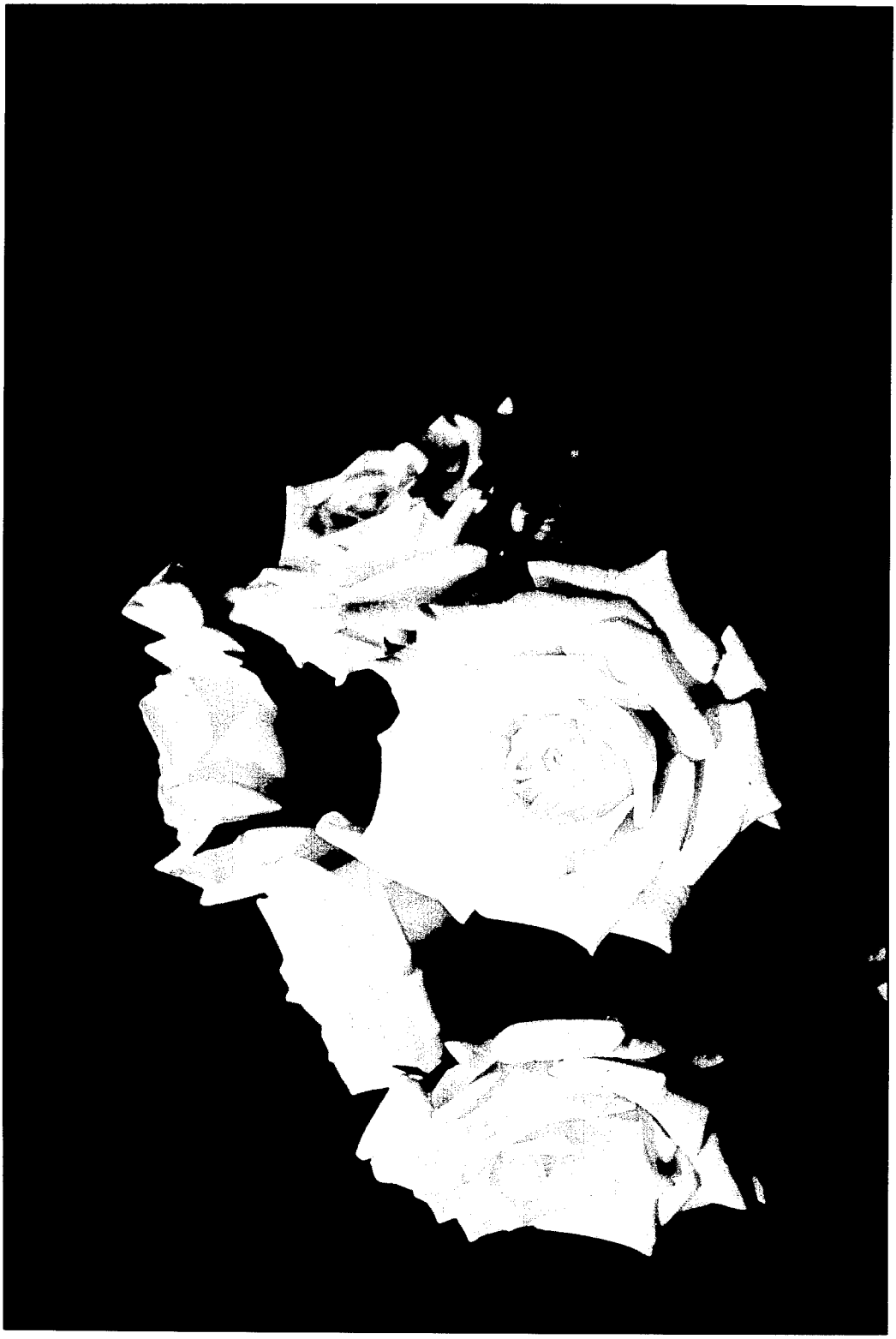

* * * * *